US008630016B2

(12) United States Patent
Swenson et al.

(10) Patent No.: US 8,630,016 B2
(45) Date of Patent: Jan. 14, 2014

(54) LABEL PROCESSOR AND METHOD RELATING THERETO

(75) Inventors: Kirk D. Swenson, North Caldwell, NJ (US); Robert S. Golabek, Jr., Towaco, NJ (US); Yuguang Wu, Montvale, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 611 days.

(21) Appl. No.: 12/278,671

(22) PCT Filed: Feb. 8, 2007

(86) PCT No.: PCT/US2007/003439
§ 371 (c)(1),
(2), (4) Date: Oct. 14, 2009

(87) PCT Pub. No.: WO2007/092587
PCT Pub. Date: Aug. 16, 2007

(65) Prior Publication Data
US 2010/0067024 A1    Mar. 18, 2010

Related U.S. Application Data

(60) Provisional application No. 60/771,923, filed on Feb. 8, 2006.

(51) Int. Cl.
    *H04N 1/00*      (2006.01)
    *B41J 11/00*      (2006.01)
    *B41J 11/50*      (2006.01)

(52) U.S. Cl.
    USPC .......... 358/1.6; 400/615.2; 400/621; 600/584

(58) Field of Classification Search
None
See application file for complete search history.

(56) References Cited

U.S. PATENT DOCUMENTS

| 3,266,298 A | 8/1966 | Whitehead et al. |
| 3,482,082 A | 12/1969 | Isreeli |
| 3,553,041 A | 1/1971 | Von Hofe |

(Continued)

FOREIGN PATENT DOCUMENTS

| EP | 510615 A1 | 4/1992 |
| EP | 0486059 B1 | 1/1997 |

(Continued)

*Primary Examiner* — Marivelisse Santiago Cordero
*Assistant Examiner* — Moustapha Diaby
(74) *Attorney, Agent, or Firm* — The Webb Law Firm

(57) ABSTRACT

A system and method are provided for providing information on at least one container for storing a biological sample, including: a holder configured to hold at least one biological sample container and a receiver configured to receive information relating to at least one of the container or the biological sample as well as data relating to at least one instruction for printing the information. The system and method further include a printer configured to print the information in accordance with the at least one instruction. In one embodiment, the printer is configured to print the information directly on the container. In another embodiment, the system and method further include an applicator configured to apply a label on the container and the printer is configured to print the information on the label. In another embodiment, the system and method include a detector configured to detect whether the container contains the biological sample and a processor configured to determine the manner for printing the information. In this embodiment, the determination is based, at least in part, on whether container contains the biological sample.

18 Claims, 8 Drawing Sheets

(56) References Cited

U.S. PATENT DOCUMENTS

| | | |
|---|---|---|
| 3,619,568 A | 11/1971 | Taplin |
| 3,653,176 A | 4/1972 | Gess |
| 3,656,473 A * | 4/1972 | Sodickson et al. ............ 600/584 |
| 3,843,440 A | 10/1974 | Davies |
| 3,898,433 A | 8/1975 | Sallet |
| 3,985,605 A | 10/1976 | Treiber et al. |
| 4,292,916 A | 10/1981 | Bradley et al. |
| 4,589,141 A | 5/1986 | Christian et al. |
| 4,626,314 A | 12/1986 | Wesley |
| 4,654,127 A | 3/1987 | Baker et al. |
| 4,828,716 A | 5/1989 | McEwen et al. |
| 5,025,798 A | 6/1991 | Schindele |
| 5,143,084 A | 9/1992 | Macemon et al. |
| 5,150,795 A | 9/1992 | Nakayama |
| 5,220,302 A | 6/1993 | Nunnally et al. |
| 5,401,110 A * | 3/1995 | Neeley ..................... 400/621 |
| 5,633,835 A | 5/1997 | Haas et al. |
| 5,688,361 A | 11/1997 | Itoh |
| 5,743,861 A | 4/1998 | Columbus et al. |
| 5,971,941 A | 10/1999 | Simons et al. |
| 6,017,318 A | 1/2000 | Gauthier et al. |
| 6,335,692 B1 | 1/2002 | Compton |
| 6,373,786 B1 | 4/2002 | Kagan et al. |
| 6,391,262 B1 | 5/2002 | Brinton et al. |
| 6,533,015 B1 | 3/2003 | Moore |
| 2001/0049147 A1 * | 12/2001 | Bierre et al. ............... 436/165 |
| 2003/0235119 A1 | 12/2003 | Wien et al. |
| 2004/0171168 A1 | 9/2004 | Itoh |
| 2004/0176704 A1 | 9/2004 | Stevens |
| 2004/0257918 A1 | 12/2004 | Ribi |

FOREIGN PATENT DOCUMENTS

| | | |
|---|---|---|
| EP | 0992287 A2 | 4/2000 |
| EP | 1004359 A2 | 5/2000 |
| JP | 1-156667 A | 6/1989 |
| JP | 3041365 A2 | 2/1991 |
| JP | 03-063570 A | 3/1991 |
| JP | 4-63484 U | 5/1992 |
| JP | 05-095936 A | 4/1993 |
| JP | 5097133 | 4/1993 |
| JP | 5-71792 U | 9/1993 |
| JP | 6-59937 | 8/1994 |
| JP | 07-167716 A | 7/1995 |
| JP | 9-504608 A | 5/1997 |
| JP | 9-236608 A | 9/1997 |
| JP | 2002-82120 A | 3/2002 |
| JP | 2002-102210 A | 4/2002 |
| JP | 2002-243734 A | 8/2002 |
| JP | 2003-004875 A | 1/2003 |
| JP | 2004-121704 A | 4/2004 |
| JP | 2004-347376 A | 12/2004 |
| WO | 01/26993 A1 | 4/2001 |
| WO | 02/06904 A1 | 1/2002 |
| WO | 2005/116632 A2 | 12/2005 |

* cited by examiner

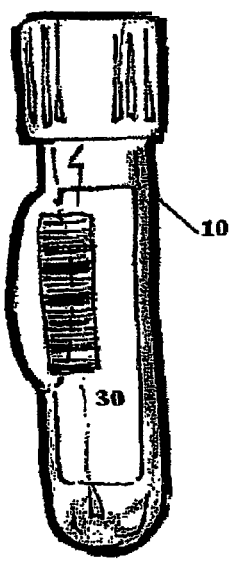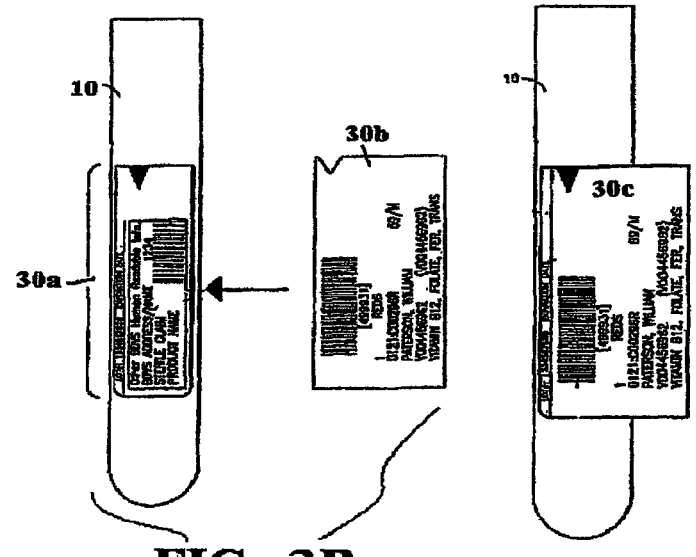
FIG. 3A  FIG. 3B  FIG. 3C

LABEL PROCESSOR AND METHOD RELATING THERETO

FIELD OF THE INVENTION

The present invention relates to labeling for laboratory related products, including but not limited to, biological sample collection containers and other biological sample collection vessels.

BACKGROUND

Labeling specimen container devices are well-known in the art for careful placement and alignment of a primary label onto a container for automated manufacturing. Additionally, some labeling machines are capable of affixing onto a container a label that is specific to a patient, specific to a type of tube, or combinations of both. Examples of known label affixation techniques include those described in the following documents including EP 510615A1 to Neeley; JP 3041365A2; JP 5097133A; U.S. Pat. No. 3,553,041 to Von Hofe; U.S. Pat. No. 3,653,176 to Gess; U.S. Pat. No. 3,843,440 to Davies; U.S. Pat. No. 3,898,433 to Sallet; U.S. Pat. No. 3,985,605 to Treiber et al.; U.S. Pat. No. 4,589,141 to Christian et al.; U.S. Pat. No. 4,626,314 to Wesley; U.S. Pat. No. 4,828,716 to McEwen et al.; U.S. Pat. No. 5,025,798 to Schindele; U.S. Pat. No. 5,150,795 to Nakayama et al; U.S. Pat. No. 5,688,361 to Itoh; and U.S. Pat. No. 6,533,015 to Moore.

While these devices handle certain labeling functions, these devices are lacking flexibility for outputting (i.e., placement) information in connection with the specimen container. Such flexibility is based upon physical attributes of the container and/or responsive to practices of the healthcare professionals handling the container. Nevertheless, improvements to the above references are always desired.

SUMMARY OF THE INVENTION

The present invention relates to an improved technique for providing information onto or into a container prior to or after the container is used as a biological specimen collection device. In accordance with an embodiment of the invention, a system and method are provided for providing information on at least one container for storing a biological sample including a holder configured to hold at least one biological sample container and a receiver configured to receive information relating to at least one of the container or the biological sample, as well as data relating to at least one instruction for printing the information. The system and method further include a printer configured to print the information in accordance with the at least one instruction.

In one embodiment, the printer is configured to print the information directly on the container. In another embodiment, the system and method further include an applicator configured to apply a label on the container and the printer is configured to print the information on the label. In another embodiment, the system and method include a printer to first print the information on a label and then with an applicator, apply the label on the container. In yet a further embodiment, the positioning of the printed label is influenced by the interpretation of information specific to the container.

In another embodiment, the system and method include a detector configured to detect whether the container contains the biological sample and a processor configured to determine the manner for printing the information. In this embodiment, the determination is based, at least in part, on whether the container contains the biological sample.

In another embodiment, the system and method include a processor configured to determine the manner for printing the information. In this embodiment, the instruction relates to, at least in part, whether the container contains the biological sample and the determination is based, at least in part, on whether container contains the biological sample.

In another embodiment, the system and method include a processor configured to determine information specific to a patient, determine the type of container to be labeled, position a label onto the container based on the determination of container type, and print information related to the patient on the label, wherein the printing of information related to the patient can occur before or after the positioning of the label onto the container.

BRIEF DESCRIPTION OF THE DRAWINGS

FIGS. 3a, 3b, and 3c illustrate side views of a container that is labeled by the machine illustrated in FIGS. 1, 2, and 5 in accordance with embodiments of the present invention;

FIG. 5a illustrates a perspective view of a labeling processing machine in accordance with an embodiment of the invention;

FIG. 5b illustrates an additional perspective view of the embodiment illustrated in FIG. 5a;

DETAILED DESCRIPTION

An evacuated container (or test tube) 10 is fed into a label processing machine 20, which operates to apply, or optionally scan/read and then apply a label onto the container in the laboratory setting. The processing machine 20 facilitates labeling of containers 10, which have been used or will be used in the process of collecting blood or specimens from a patient and eventually transferred to a diagnostic system (not shown), such as an analyzer, for subsequent analysis.

Figure 1:
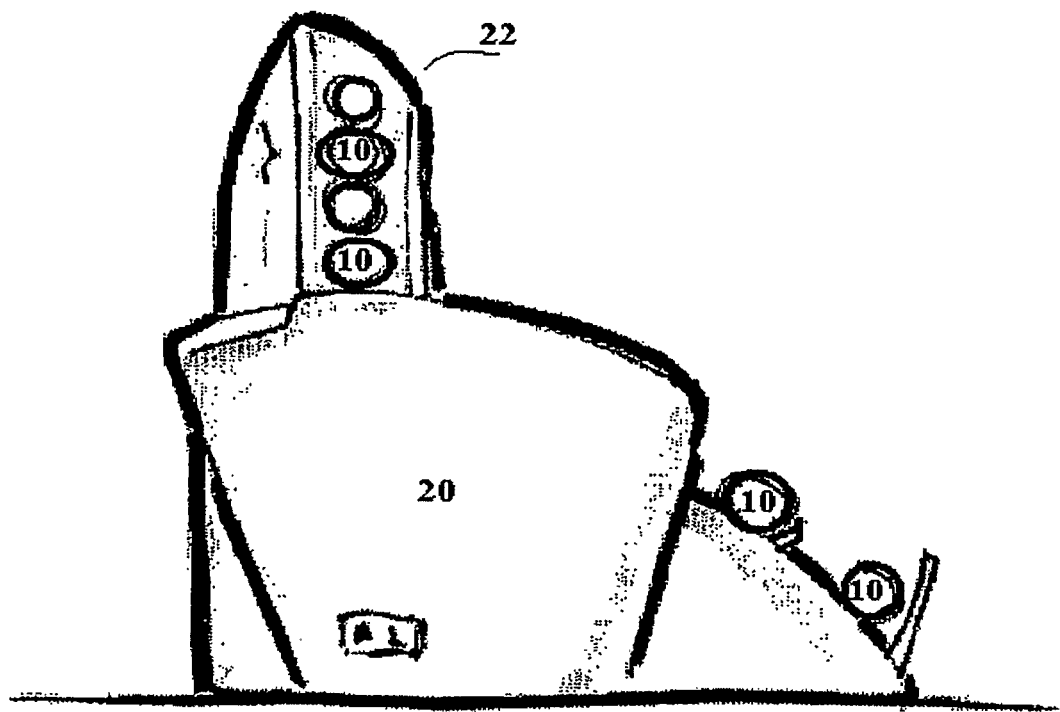
FIG. 1 illustrates a side view of a labeling processing machine, in accordance with an embodiment of the invention.
Figure 2:
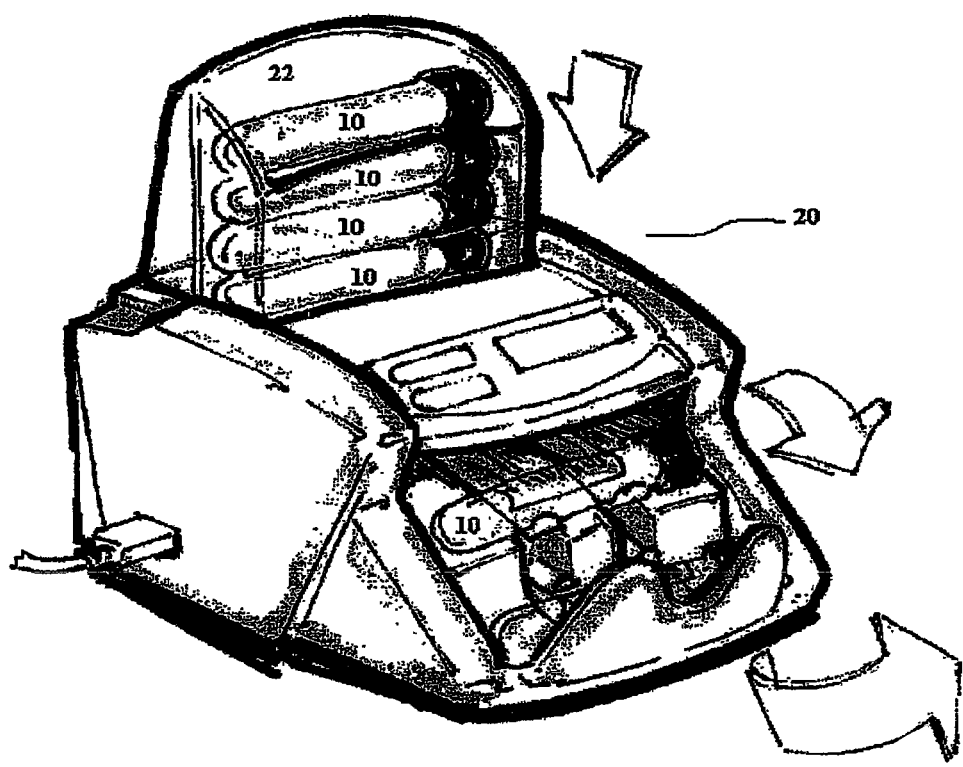
FIG. 2 illustrates a perspective view of the embodiment of FIG. 1.
Figures 5A, 5B:
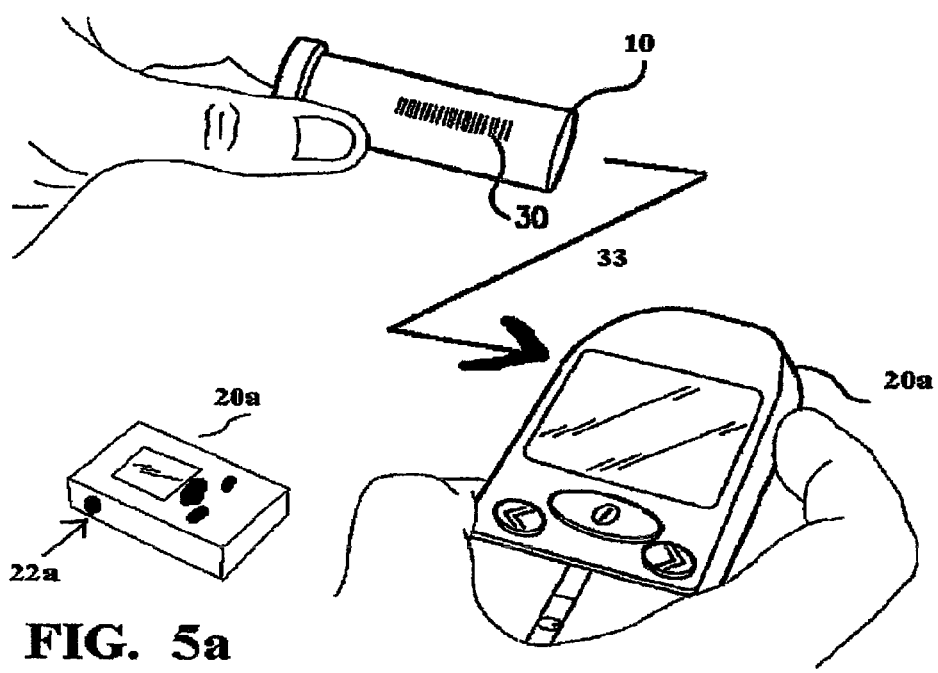

The label processing machine 20 generally comprises a hopper 22, a holder for holding a roll of labels 29 comprising roll paper 31 with removably attached thereto a plurality of labels 30, a printer (not shown) within a machine 20 for printing (i.e., onto a label 30, a container 10, or both), optionally a scanner for scanning indicia (i.e., on the label 30, container 10, or patient ID, health practitioner ID, etc.), and alignment elements to facilitate alignment of labels 30 applied to the container 10. A controller and/or processor are incorporated to directly or indirectly instruct portions of the label-processing machine 20 to enable appropriate printing, scanning, and label application to objects fed into the hopper 22. The containers 10 can be placed into the hopper 22 and indexed by a controller that enables selective positioning of the container 10 into an appropriate position to be labeled by the label-processing machine 22. The hopper 22 of the label processing machine 20 accepts collection containers 10 of either similar or various diameter and length product variations. Optionally as shown in machine 20a, the hopper may be designed to accept only one collection container at a time such as that shown in FIGS. 5a and 5b. For instance, hopper 22a of machine 20a in FIGS. 5a and 5b receives one tube at a time, wherein insertion of the container 10 into the hopper 22a by motion along for instance path 33 enables either one or both of determining information about the container or a patient, and printing information related to the container or patient on the collection container 10. As shown in the FIGS. 1 and 2, the hopper 22 may accept a plurality of containers 10 stacked such that one container 10 at a time enters into a labeling, scanning, or printing zone within the label processing machine 20.

In an embodiment, the label-processing machine 20 may read or scan through the sidewall of the transparent glass or plastic container 10 and determine if the container 10 has been filled with a sample or fluid specimen, and thereby incorporate that information into a decision of whether or not to label the container 10, or optionally determine how to label the container 10. In another embodiment of the label processing machine 20, the machine 20 may read or scan the container 10 to see whether indicia is associated with the container 10 such that the machine can identify information about the container 10 that may facilitate what information is to be printed onto the container 10, either directly onto a label pre-applied to the container 10, directly onto the container 10 itself, or optionally indirectly by printing onto a label 30 that is applied to the container 10 by the label processing machine 20.

In another embodiment of the invention, the label processing machine 20 interprets for a remote source information that influences or informs the label processing machine 20 on how and to what information should be printed. For example, a remote source can be a laboratory information system that may communicate directly or indirectly with the label processing machine 20 to inform what should be printed onto the container 10. In some embodiments of the present invention, scanning of the container 10 to compare information about the container 10 with that from a remote source (i.e., an LIS system or user input module) is required. In other embodiments, scanning and/or comparing information is not required.

In an embodiment of the invention, it is desirable to achieve alignment and positioning improvement of labels 30 onto the container 10. In one embodiment of the invention, the label is positioned purposefully in a position with respect to a label 30 already applied to a container 10. It should be noted that it may be desirable to label a container 10 already labeled such that the second label is an over-label applied by the machine 20 to the container 10. Additionally, it may be desirable to radially align a portion of the label 30 to either a radial datum on the container 10, or optionally, a readable portion of a first label (under-label). Additionally, the label processing machine 20 may comprise a scanner that reads information about the container 10 or any label 20 attached thereto wherein the scanner moves or rotates relative to the container 10, such that the container 10, scanner, or both may be fixed or rotated to achieve such relative movement.

In another embodiment of the label processing machine 20, a label 30 may be applied in a variety of manners. For example, an adhesive backed label may be used, wherein the adhesive backed label is pre-applied to a roll 29 which is placed into the machine's label applicator portion. The label applicator portion comprises rollers (not shown) that rotate the label roll 29, the container 10, or both such that individual labels are peeled from the roll 29 and purposefully applied to the container in a desired manner. The output of the machine 20, in accordance with an embodiment of the invention, is illustrated by the tube and label shown in FIGS. 3a, 3b, and 3c.

Figure 4:
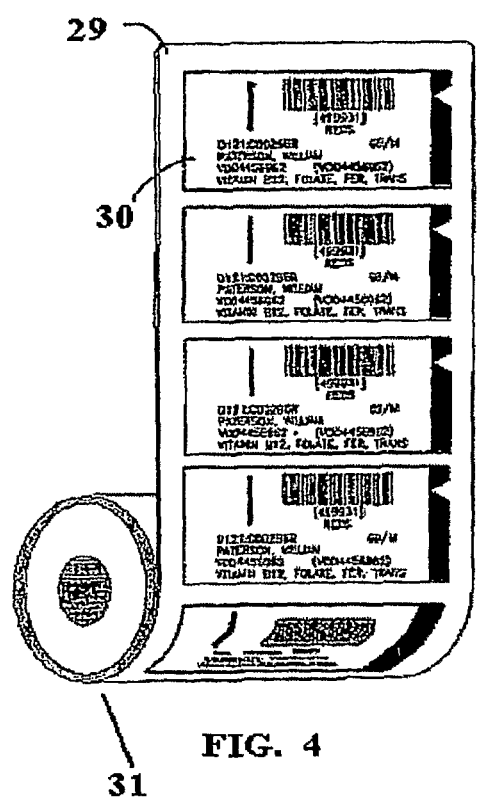
FIG. 4 illustrates a perspective view of a label roll in accordance with embodiments of the present invention.
Figure 6:
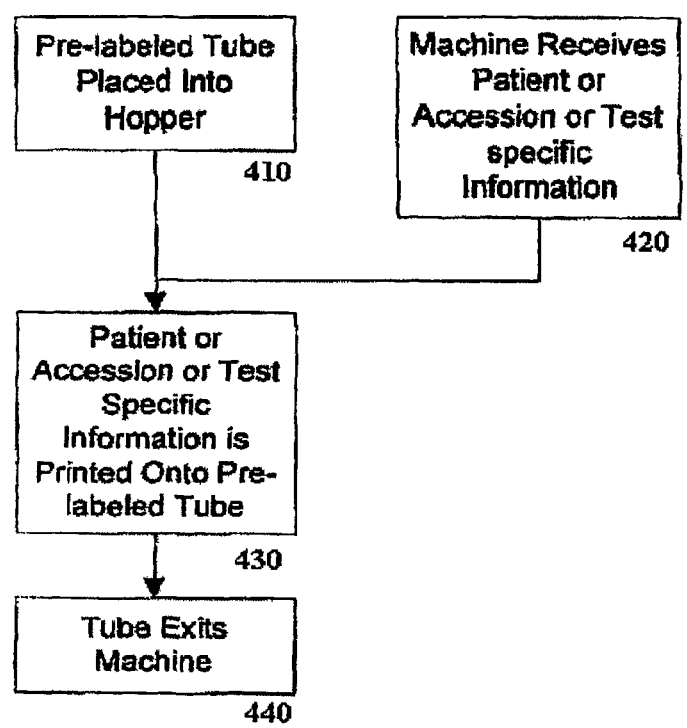
FIG. 6 illustrates a diagram depicting a process for labeling a container in accordance with an aspect of the present invention.

FIG. 3a demonstrates a label applied to container 10 demonstrated in embodiments of the invention. FIG. 3b demonstrates two labels 30a and 30b, one (30a) of which is pre-applied to the container 10 first, and label 30b that is later applied to the container 10 by applying at least a portion of label 30b onto at least a portion of label 30a, thereby producing an overlabel subassembly 30c shown in FIG. 3c. The shape, design, size, and material choice of labels 30a and 30b are chosen such that upon correct and intended positioning of label 30b with respect to label 30a by machine 20 and 20a, portions of label 30a are possible to be seen visually as per design and positioning of label 30a indicia. In FIGS. 4 to 6 (with reference to FIGS. 1 to 3), the system and method for using the present invention is illustrated. As depicted in FIG. 6, one or multiple tubes or containers 10 (hereinafter also referred to as vessels) are loaded into the hopper 20 (step 410). The label-processing machine 20 receives information that relates to the information that is printed onto the vessels directly or indirectly and the manner for effectuating such printing (step 420). The label processing machine 20 may receive information in a variety of ways, including but not limited to: from keyed user input, by accessing a database of information remote from or integral to the label processor, from a wireless or wired telecommunications connection, from data communicated by scanning scannable information (i.e., barcode RFID, 1D, or 2D barcode scanner on the vessel itself or on a patient's wristband, patient chart, or other related scannable apparatus). An algorithm accessible by label processing machine 20 incorporates the received information and prints information onto the container 10 or label 30 pre-applied to the container (step 430). Container 10 is then positioned to exit machine 20 (step 440).

Figure 7:
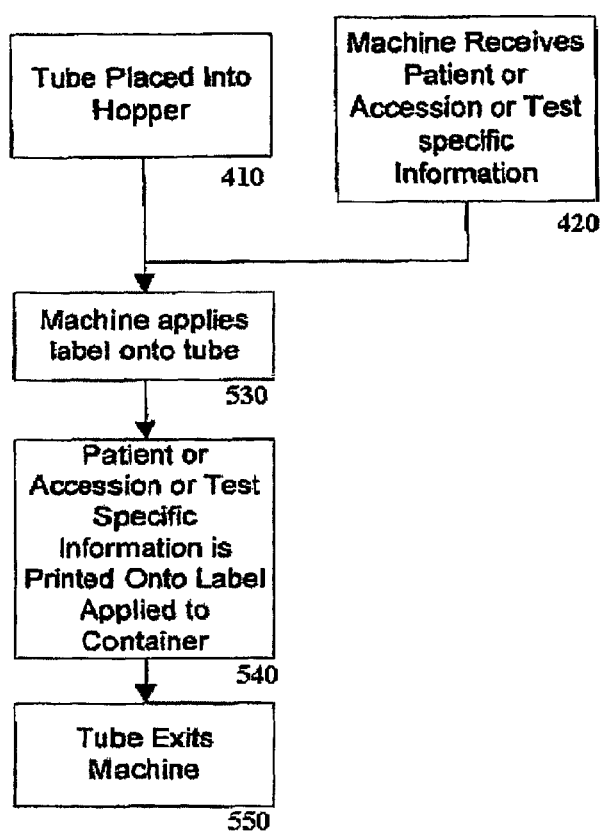
FIG. 7 illustrates a diagram depicting a process for labeling a container in accordance with another aspect of the present invention.

As illustrated in FIG. 7, the label-processing machine 20 operates similar to FIG. 6 with the exception that the machine 20 first applies label 30 onto the vessel 10 (either onto a label-less vessel or onto a vessel that already has a label applied thereto (30a)) (step 530), and subsequently prints specific information onto recently-applied label (30b when 30a is used as in FIGS. 3b and 3c) (step 540). Vessel 10 is then positioned to exit machine 20 (step 550).

Figure 8:
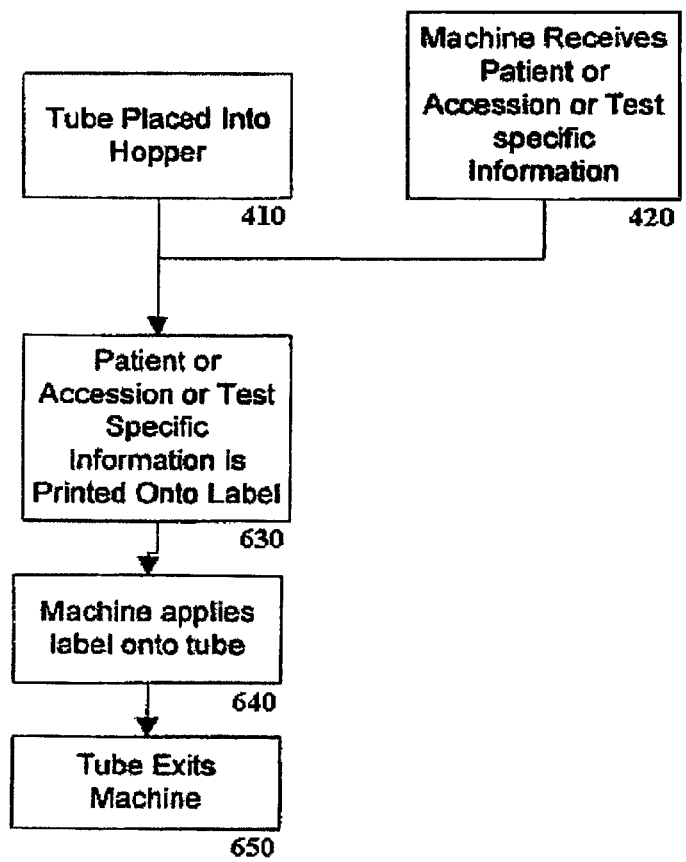
FIG. 8 shows a diagram depicting a process for labeling a container in accordance with yet another aspect of the present invention.

As illustrated in FIG. 8, the label-processing machine 20 operates similar to FIG. 7 with the exception that the machine 20 first prints onto label 30 (step 630), and then applies label 30 onto vessel 10 (step 640). Vessel 10 is then positioned to exit machine 20 (step 650).

Aspects of the invention may be used with vessels that have already been filled with a sample specimen or may be used with vessels that have not already been filled with a sample specimen. The processor can be programmed to accommodate both of these scenarios.

While the present invention is satisfied by embodiments in many different forms, there is shown in the figures and described herein in detail, various embodiments of the invention, with the understanding that the present disclosure is to be considered as exemplary of the principles of the invention and is not intended to limit the invention to the embodiments illustrated. Various other embodiments will be apparent to, and readily made by those skilled in the art, without departing from the scope and spirit of the invention. The scope of the invention will be measured by the appended claims and their equivalents.

What is claimed:

1. A system for providing information on at least one container for storing a biological sample, comprising:
   a holder configured to hold at least one biological sample container;
   a receiver configured to receive:
      information relating to at least one of the container or the biological sample; and
      data relating to at least one instruction for printing the information;
   a printer configured to print the information in accordance with the at least one instruction;
   an applicator configured to apply a label on the container;
   a detector configured to detect whether the container contains the biological sample; and
   a processor configured to determine the manner for printing the information, wherein the determination is based, at least in part, on whether the container contains the biological sample.

2. The system of claim 1, wherein the printer is configured to print the information directly on the container.

3. The system of claim 1, wherein the printer is configured to print the information on the label.

4. The system of claim 3, wherein the printer is configured to print the information on the label after the applicator applies the label to the container.

5. The system of claim 1, wherein the instruction relates to, at least in part, whether the container contains the biological sample.

6. The system of claim 1, wherein the instruction relates, at least in part, to orientation for printing the information by the printer.

7. The system of claim 1, wherein the data relates, at least in part, to placement of the information by the printer.

8. The system of claim 1, wherein the data relates, at least in part, to orientation of the container in the system.

9. The system of claim 1, wherein the data relates, at least in part, to the placement of the container in the system.

10. A method for providing information on at least one container for storing a biological sample, comprising:
    holding the at least one biological sample container by an apparatus having printing capability and an applicator configured to apply a label on the container;
    receiving information relating to at least one of the container or the biological sample, and data relating to at least one instruction for printing the information;
    printing the information, by the apparatus, in accordance with the at least one instruction;
    detecting whether the container contains the biological sample; and
    determining the manner for printing the information, wherein the determining is based, at least in part, on whether the container contains the biological sample.

11. The method of claim 10, wherein the information is printed directly on the container.

12. The method of claim 10, further comprising: applying a label on the container, and wherein the information is printed on the label.

13. The method of claim 12, wherein the information is printed on the label after the applicator applies the label to the container.

14. The method of claim 10, wherein the instruction relates to, at least in part, whether the container contains the biological sample.

15. The method of claim 10, wherein the instruction relates, at least in part, to orientation for printing the information.

16. The method of claim 10, wherein the data relates, at least in part, to placement of the information.

17. The method of claim 10, wherein the data relates, at least in part, to orientation of the container for the printing.

18. The method of claim 10, wherein the data relates, at least in part, to the placement of the container for the printing.

* * * * *

UNITED STATES PATENT AND TRADEMARK OFFICE
CERTIFICATE OF CORRECTION

PATENT NO. : 8,630,016 B2  Page 1 of 1
APPLICATION NO. : 12/278671
DATED : January 14, 2014
INVENTOR(S) : Swenson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1155 days.

Signed and Sealed this
Twenty-second Day of September, 2015

Michelle K. Lee
*Director of the United States Patent and Trademark Office*